United States Patent [19]
Bather

[11] Patent Number: 4,820,920
[45] Date of Patent: Apr. 11, 1989

[54] METHOD AND APPARATUS FOR DETECTING DANGEROUS SUBSTANCES

[75] Inventor: John M. Bather, Prestbury, United Kingdom

[73] Assignee: Analytical Security Systems Limited, Manchester, United Kingdom

[21] Appl. No.: 43,905

[22] Filed: Apr. 24, 1987

[51] Int. Cl.$^4$ .............................................. B01D 59/44
[52] U.S. Cl. ...................................... 250/282; 250/288
[58] Field of Search ................... 250/252.1, 282, 288, 250/425, 289

[56] References Cited

U.S. PATENT DOCUMENTS

| | | | |
|---|---|---|---|
| 2,714,164 | 7/1955 | Riggle et al. | 250/289 |
| 3,476,968 | 11/1969 | Omura | 250/425 |
| 3,867,631 | 2/1975 | Briggs | 250/288 |
| 3,920,987 | 11/1925 | Anbar et al. | 250/282 |
| 3,999,065 | 12/1976 | Briggs | 250/288 |
| 4,167,667 | 9/1979 | Hall | 250/288 |
| 4,260,886 | 4/1981 | Grilletto et al. | 250/288 |
| 4,314,156 | 2/1982 | Kuppermann | 250/282 |
| 4,442,353 | 4/1984 | Baubron | 250/288 |

Primary Examiner—Bruce C. Anderson
Attorney, Agent, or Firm—Robert W. Fiddler

[57] ABSTRACT

A method of detecting a dangerous substance such as explosives or drugs in an article (27) in transit comprises the steps of taking a sample of atmosphere (28) from the vicinity of the article, causing the sample to enter an ionization chamber (24) of a mass spectrometer (30), obtaining a mass spectrum of one or more constituents of the sample, comparing the mass spectrum with one or more reference spectra, and generating a signal indicative of any said dangerous substance in the sample.

6 Claims, 6 Drawing Sheets

METHOD AND APPARATUS FOR DETECTING DANGEROUS SUBSTANCES

TECHNICAL FIELD

This invention relates to a method and apparatus for detecting dangerous substances such as explosives, controlled substances or inflammable substances. The invention finds particular but not exclusive application in screening of articles such as baggage, freight or clothing in transit for example before or during transportation in aircraft or shipping.

BACKGROUND ART

Conventional methods of detection of dangerous substances include use of flame ionisation chromatography or other chromatographic techniques. These methods are prone to false alarms and have the additional disadvantage that a substance detected is not identified chemically.

DISCLOSURE OF THE INVENTION

According to a first aspect of the present invention a method of detecting a dangerous substance in an article in transit comprises the steps of taking a sample of atmosphere from the vicinity of the article, causing the sample to enter an ionisation chamber of a mass spectrometer, obtaining a mass spectrum of one or more constituents of the sample, comparing the mass spectrum with one or more reference spectra, and generating a signal indicative of any said dangerous substance in the sample.

Use of mass spectrometry for detection of explosives, controlled substances, inflammable or other hazardous substances is advantageous in that the chemical identity of any such substance can be determined from the fragmentation pattern of the mass spectrum. This serves to reduce the likelihood of a false alarm, such as might occur when using a technique dependent simply on retention times on a chromatographic column. For example, foodstuffs containing vinegar have been found to activate a flame ionisation chromatograph arranged to detect explosives.

In a particularly preferred method a sample is taken of atmosphere in a compartment in an aircraft, ship, vehicle or other means of transportation.

Sampling means may be permanently disposed in the compartment, affording means of detection of any dangerous substances which might be placed in the compartment. Compartments in which sampling means may be disposed include not only storage compartments such as holds, loading bays, containers or the like, but also compartments which might be used for unauthorised storage of contraband such as wheel cavities or toilets of aircraft.

A preferred method may include the steps of:
exposing the article to microwave or radio frequency radiation to vaporise a component of said dangerous substance;
removing a sample of vapour from the vicinity of the article; and
causing the sample to enter an ionisation chamber of a mass spectrometer.

A multiplicity of sampling means located at various locations in an aircraft, vessel or vehicle may be arranged to deliver samples of atmosphere to a single mass spectrometer.

According to a second aspect of the present invention dangerous substance detecting apparatus may comprise sampling means arranged to take a sample of atmosphere from the vicinity of an article in transit, a mass spectrometer means arranged to cause the sample to enter an ionisation chamber of the mass spectrometer, means arranged to compare a mass spectrum generated by the mass spectrometer with one or more reference spectra and a signal generator arranged to generate a signal indicative of any said dangerous substance in the sample.

The sampling means may comprise a capillary needle probe. Alternatively, the sampling means may comprise a porous diaphragm such as a metallic frit.

The apparatus may incorporate means arranged to irradiate a sample with microwave or radio frequency radiation and means arranged to collect a sample of vapour from the vicinity of the sample. The frequency of the radiation is preferably selected to cause vapourisation of predetermined compounds or components of substances which exhibit mass spectra characteristic of the presence of dangerous substances.

A preferred apparatus for checking luggage or other portable articles may comprise a tunnel or other passageway arranged to be sealed to form a compartment enclosing a said article. Microwave generating apparatus is arranged to allow a pulse of radiation into the compartment to vapourise any dangerous substance contained within the article. Automatic vapour phase sampling equipment in the compartment may then be actuated to withdraw a sample from the compartment for analysis by a mass spectrometer. A preferred type of vapour phase sampling equipment is that used for hermetic packaging of foodstuffs, such equipment having a facility to rapidly and repeatedly evacuate a compartment so that a large number of rapidly successive operations may be performed. Alternative sampling apparatus may be employed.

One or more sampling means may be connected to the inlet of a mass spectrometer by tubing such as a vacuum line.

A quadropole mass spectrometer or other suitable mass spectrometer with a multi channel inlet is preferred.

A microprocessor may be arranged to compare the mass spectrum with reference spectra. The reference spectra may comprise spectra of non-dangerous substances, any compound not falling within the reference spectra causing an alarm signal to be generated. Alternatively, or in addition an alarm may be generated upon detection of any known dangerous substances.

Apparatus having one or more portable detectors may be used to screen individual items of baggage etc. Alternatively, fixed detectors may be located in compartments to detect any dangerous substances placed therein.

The method and apparatus of this invention are particularly beneficial in that a constantly active means of detection may be provided. Thus aircraft may be protected from terrorist attacks during flight. In addition there is no need for passage of all baggage etc., through a checkpoint prior to loading. This avoids the possibility that arms, bombs etc., could be smuggled onto an aircraft by crew members, airport personnel or other persons who are not subject to rigorous customs scrutiny. Confidence of crew members and passengers is enhanced and insurance premiums may be reduced.

The method has the additional advantage that atmospheric concentrations of dangerous substances may reach a threshold of detectability during prolonged storage in an enclosed or confined compartment. A permanently active detector may therefore be successful when screening prior to loading was not.

BRIEF DESCRIPTION OF THE DRAWINGS

The invention is further described by means of example and not in any limitative sense with reference to the accompanying drawings, of which.

MODES OF CARRYING OUT THE INVENTION

Figure 1:
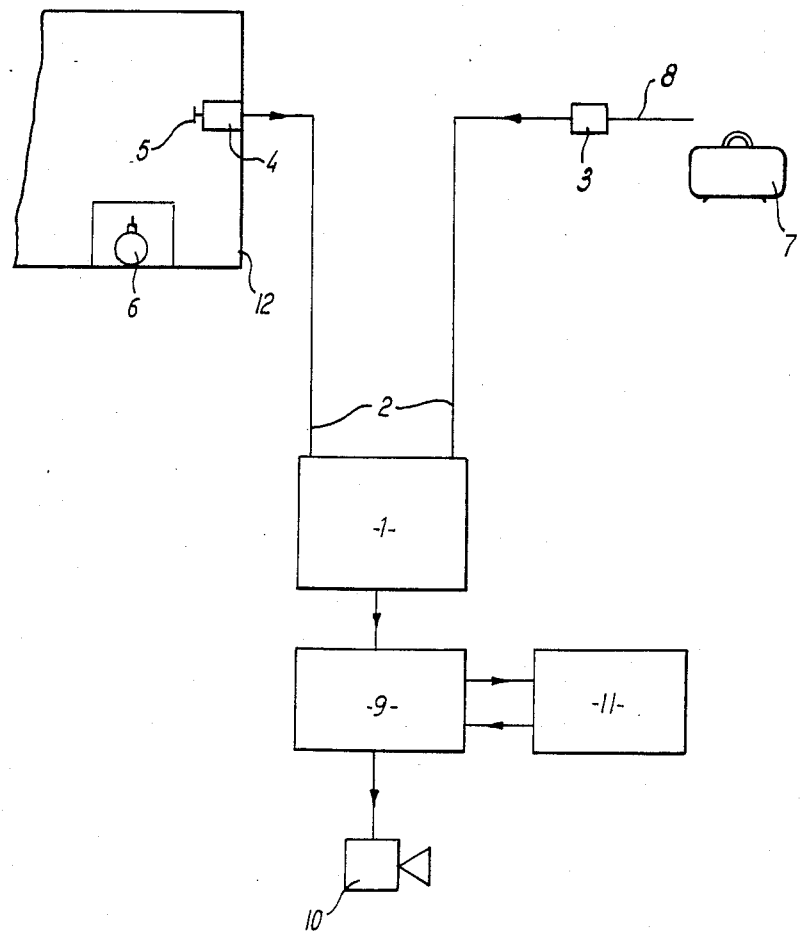
FIG. 1 is a schematic diagram illustrating apparatus in accordance with the invention.

FIG. 1 illustrates apparatus which may be permanently installed in an aircraft, ship or other means of transportation. A multichannel quadropole mass spectrometer 1 arranged to receive atmospheric samples via tubes 2 from a multiplicity of probes 3,4. A probe 3 having a capillary needle 8 may be used for inspection of baggage 7, clothing or other articles to be transported. A probe 4 located in a storage compartment 12 has a porous diaphragm 5 through which atmospheric samples are continuously taken. Traces of explosives from a bomb 6 concealed in the storage compartment may build up during transportation causing activation of the alarm.

The digital output of the mass spectrometer 1 is compared by a microprocessor 9 with reference spectra contained in a disc store 11. Presence of any previously known dangerous substances or of any unidentified substances causes a signal to be sent to an alarm 10.

Figure 2:
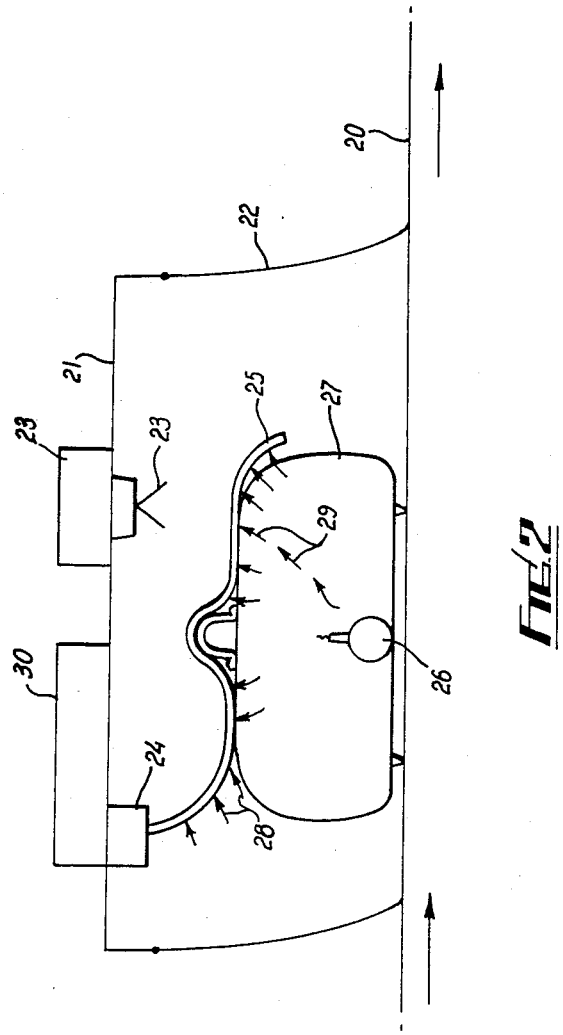
FIG. 2 is a perspective view of apparatus in accordance with this invention.

In an alternative embodiment a probe may be located in a tunnel or other chamber containing a source of microwaves or radio frequency radiation. FIG. 2 illustrates such an arrangement. A baggage handling conveyor 20 passes through a tunnel 21 having microwave proof barriers 22 at each end. A microwave generator 23 is arranged to produce pulses of radiation within the tunnel 21. A probe and mass spectrometer 30 analyse samples of air drawn from the tunnel after each irradiation. The barriers 22 may comprise curtains, screens or doors composed of perforated metal or other microwave impermeable material. A SKW microwave generator emitting 1 second pulses at 10 cm wavelength has been found to be suitable for use in conjunction with a tunnel having a volume of 1m$^3$.

The probe 24 includes a pump which draws air 28 for analysis through one or more flexible perforated tubes 25. The tube 25 is arranged to contact the surface of a suitcase 27 or other article which passes through the tunnel. The perforations may open downwardly so that air is drawn from the surface of the article 27. It is preferred that the tube 25 is arranged to engage the article by means of the partial vacuum at or adjacent the closure of the article. Vapour emitted by microwave heating of explosives 26 within the suitcase 27 is drawn 29 from the suitcase by suction from the tube 25. Alternatively the tube may be replaced by a hollow sheet or bag having downwardly opening perforations.

FIGS. 3 to 7 illustrate use of the apparatus shown in FIG. 2 for detection of explosives contained in a suitcase using a V.G.Petra mass spectrometer arranged in accordance with this invention. The most difficult explosives to detect instrumentally are plastic explosives.

Figure 3:
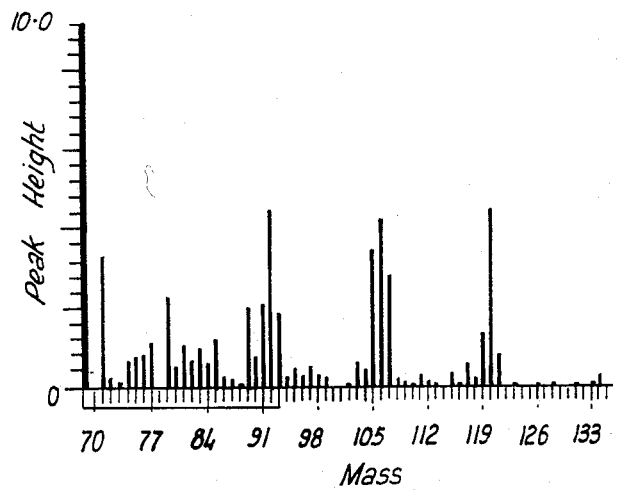
FIGS. 3 to 13 illustrate mass spectra obtained in use of the invention.
Figure 4:
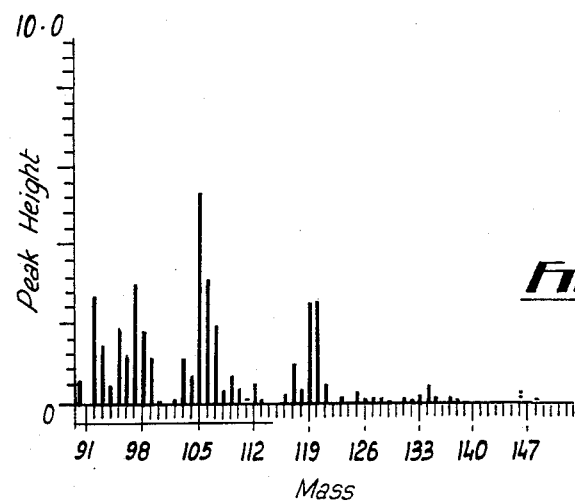
Figure 5:
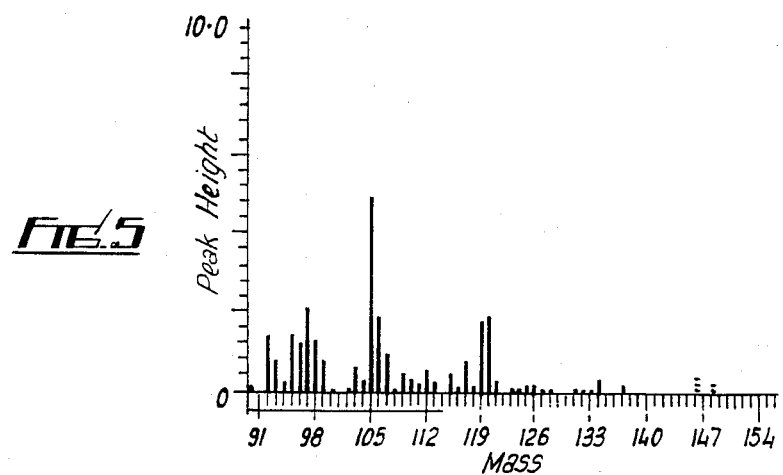
Figure 6:
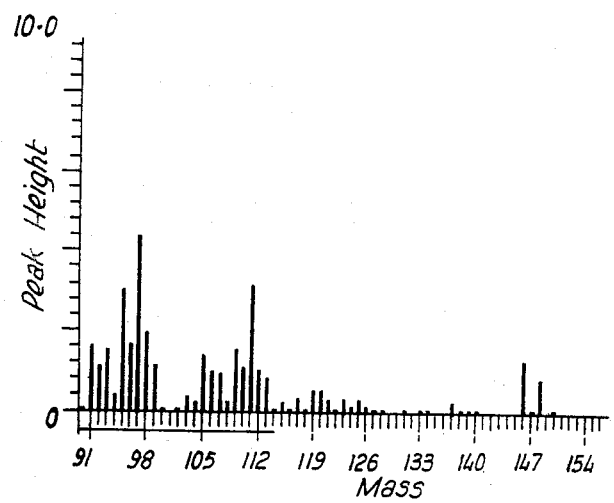
Figure 7:
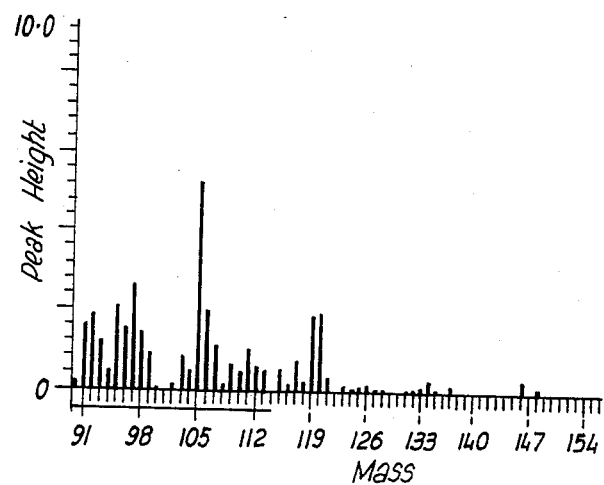

The very low vapour pressures exhibited at ambient temperatures by plastic explosives frequently do not reach the threshold above which conventional chromatographic techniques are effective. The materials commonly employed in manufacture of plastics explosives are, in order of decreasing vapour pressure (I) pentaerythritol nitrate (PEN), (II) trinitrotoluene, (III) nitroglycerine, (IV) ammonium nitrate/sugar. Experimental work has shown that all but (IV) can be detected by the method of this invention. The method is sufficiently sensitive to detect vapour from these compounds passing through five layers of polyethylene sheet. FIG. 3 shows a mass spectrum taken from an empty metal box, which had been used to store explosives. FIGS. 4 to 6 illustrate spectra obtained from the explosives: PE4; 808 and PETN respectively. FIG. 7 is a control spectrum obtained from an empty polythene bag. The spectra obtained from the different materials are different and distinctive facilitating detection and discrimination by an appropriately programmed microprocessor.

The ability to distinguish individual molecular species confers the advantage over prior art arrangements that false alarms are avoided. False alarms have been found to occur frequently with prior art arrangements.

Figure 8:
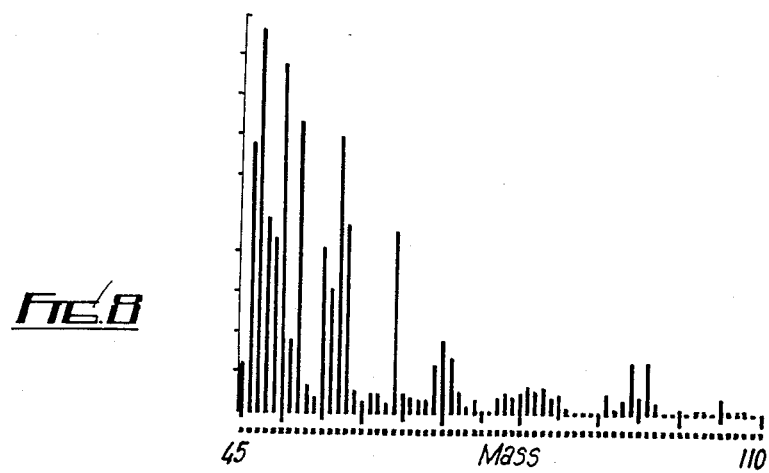
Figure 9:
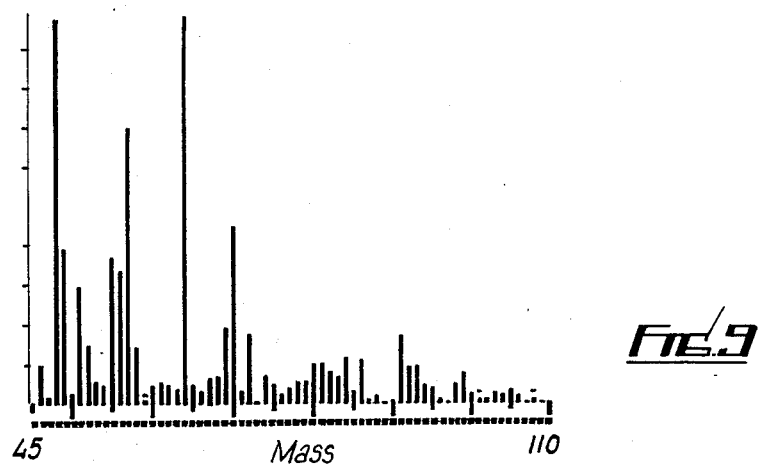
Figure 10:
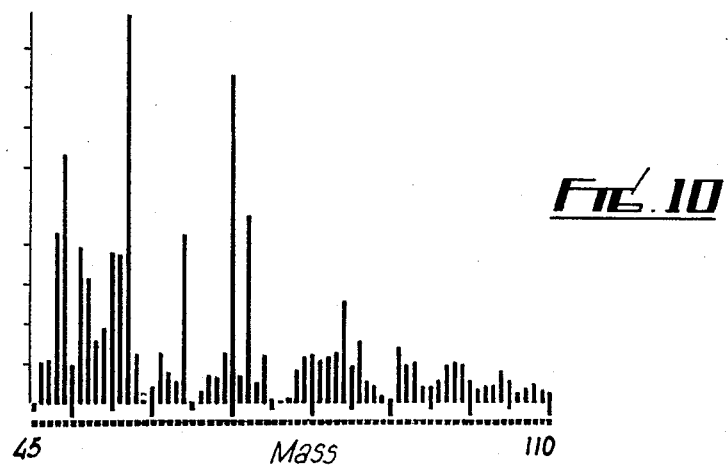
Figure 11:
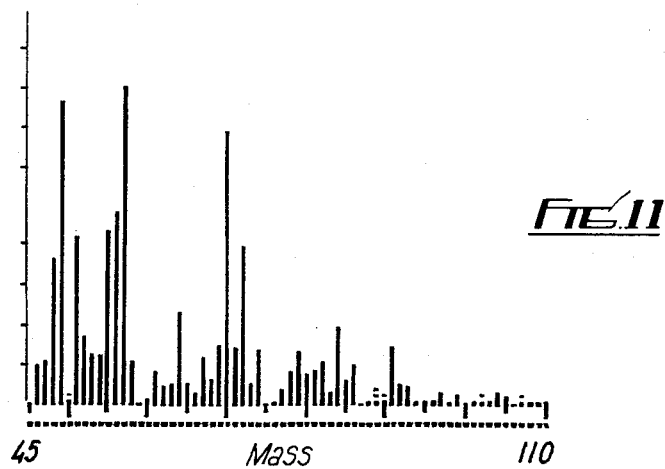
Figure 12:
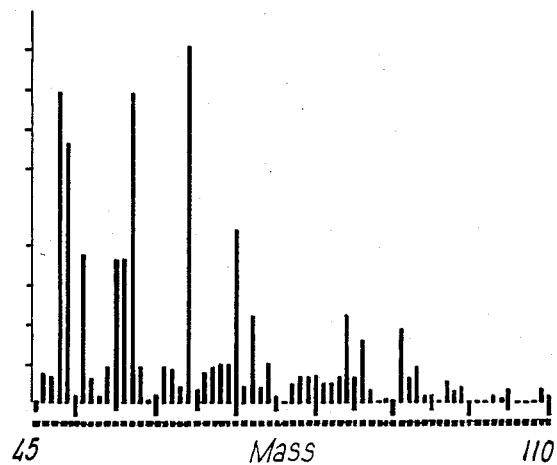
Figure 13:
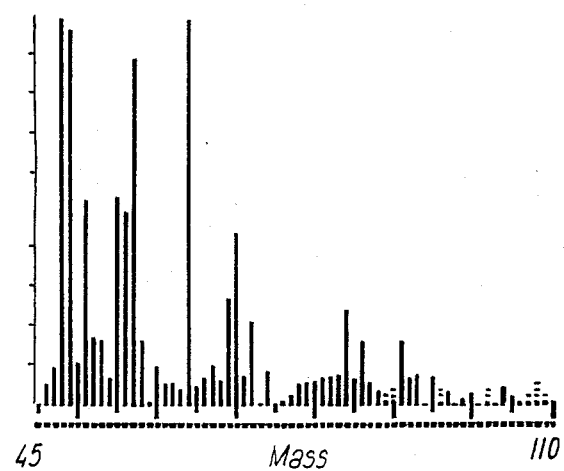

FIGS. 8 to 13 illustrate mass spectra obtained from samples of cannabis from different locations. FIG. 8 was obtained from liquid cannabis. FIGS. 9 to 13 were obtained from cannabis from Morrocco, Pakistan, Lebanon, India and Turkey respectively. Not only can these substances be detected accurately but an immediate identification of their origin provides the police or customs authorities with information which would not otherwise be immediately available.

Apparatus in accordance with this invention may be also used to detect opiates, cocaine, amphetamines or other controlled substances.

It will be appreciated by those skilled in the art that variations and modifications can be made to the invention disclosed above within the scope of the invention.

I claim:

1. A method of detecting a dangerous substance in an article in transit comprising the steps of:
   exposing the article to microwave or radiofrequency radiation to vaporize a component of said dangerous substance;
   taking a sample of vapor from the vicinity of the article;
   causing the sample to enter an ionization chamber of a mass spectrometer;
   obtaining a mass spectrum of one or more constituents of the sample;
   comparing the mass spectrum with one or more reference spectra; and
   generating a signal indicative of any dangerous substance in the sample.

2. A method as claimed in claim 1, wherein the sample is taken from a compartment of a means of transportation.

3. A method as claimed in claim 2, wherein a multiplicity of sampling means located at various locations in an aircraft, vessel or vehicle are arranged to deliver samples to a single mass spectrometer.

4. Dangerous substance detecting apparatus comprising sampling means arranged to take a sample of atmosphere from the vicinity of an article in transit, a mass spectrometer means arranged to cause the sample to enter an ionization chamber of the mass spectrometer, means arranged to compare a mass spectrum generated by the mass spectrometer with one or more reference spectra and a signal generator arranged to generate a signal indicative of any dangerous substance in the sample, wherein the sampling means includes a perforated member arranged to contact the surface of said article.

5. Apparatus as claimed in claim 4, wherein the sampling means comprises a capillary needle probe.

6. Apparatus as claimed in claim 4, wherein the sampling means comprises a porous diaphragm.

* * * * *